United States Patent
Arshava

(10) Patent No.: US 10,966,751 B2
(45) Date of Patent: Apr. 6, 2021

(54) THORACOSCOPIC IRRIGATION CANNULA

(71) Applicant: University of Iowa Research Foundation, Iowa City, IA (US)

(72) Inventor: Evgeny Arshava, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 81 days.

(21) Appl. No.: 16/253,838

(22) Filed: Jan. 22, 2019

(65) Prior Publication Data
US 2019/0223902 A1 Jul. 25, 2019

Related U.S. Application Data

(60) Provisional application No. 62/620,175, filed on Jan. 22, 2018.

(51) Int. Cl.
 *A61B 17/34* (2006.01)
 *A61B 17/02* (2006.01)

(52) U.S. Cl.
 CPC ...... *A61B 17/3421* (2013.01); *A61B 17/0293* (2013.01); *A61B 2017/0237* (2013.01); *A61B 2017/3425* (2013.01); *A61B 2017/3427* (2013.01)

(58) Field of Classification Search
 CPC .. A61M 3/0279; A61M 3/0287; A61M 27/00; A61M 3/02; A61M 3/00; A61M 1/0021; A61M 5/00; A61M 2039/0009; A61M 1/0084; A61F 5/442; A61F 5/445; A61J 1/05
See application file for complete search history.

(56) References Cited

U.S. PATENT DOCUMENTS

| | | | |
|---|---|---|---|
| 2,568,566 A * | 9/1951 | Sokolik | A61M 1/0084 604/26 |
| 2,863,444 A | 12/1958 | Winsten | |
| 5,514,076 A | 5/1996 | Ley | |
| 6,416,465 B2 | 7/2002 | Brau | |
| D511,383 S | 11/2005 | Stanger | |

(Continued)

OTHER PUBLICATIONS

Schneiter, Didier, et al. "Accelerated Treatment of Postpneumonectomy Empyema: A Binational Long-Term Study." The Journal of Thoracic and Cardiovascular Surgery, vol. 136, No. 1, Jul. 4, 2008, pp. 179-185., doi:10.1016/j.jtcvs.2008.01.036. (Year: 2008).*

(Continued)

*Primary Examiner* — Matthew J Lawson
*Assistant Examiner* — Lisa Nguyen
(74) *Attorney, Agent, or Firm* — McKee, Voorhees & Sease, PLC

(57) ABSTRACT

An irrigation cannula is provided for irrigating a chest cavity during thoracoscopic surgery. The cannula includes a bowl with a drain opening, and a hollow leg extending from the bowl beneath the drain opening. An obturator has an upper handle and a lower end which is manually pushed through the drain opening and into the leg so that a handle resides in or above the bowl and a tip extends beyond the end of the leg. The obturator facilitates insertion of the cannula leg through the incision and into the chest cavity. After the cannula is in position, an irrigation solution is added to the bowl, and drain through the leg into the chest cavity.

20 Claims, 9 Drawing Sheets

(56) References Cited

U.S. PATENT DOCUMENTS

| | | | |
|---|---|---|---|
| D724,207 S | 3/2015 | Sutherland et al. | |
| 2009/0281483 A1* | 11/2009 | Baker .................. | A61M 11/042 604/28 |
| 2013/0118639 A1* | 5/2013 | Springer .................. | B65D 1/06 141/2 |
| 2014/0121592 A1* | 5/2014 | Rubin .................. | A61M 3/0283 604/30 |
| 2015/0057678 A1* | 2/2015 | Chotenovsky ... | A61B 17/12009 606/140 |
| 2016/0130793 A1* | 5/2016 | Lesmeister .............. | A47K 1/14 4/287 |
| 2018/0162717 A1* | 6/2018 | Manwani ............... | B65D 23/02 |

OTHER PUBLICATIONS

Orringer, Mark B., "Transhiatal Esophagectomy without Thoracotomy", Operative Techniques in Thoracic and Cardiovascular Surgery, vol. 10, Issue 1, pp. 63-83, 2005.

\* cited by examiner

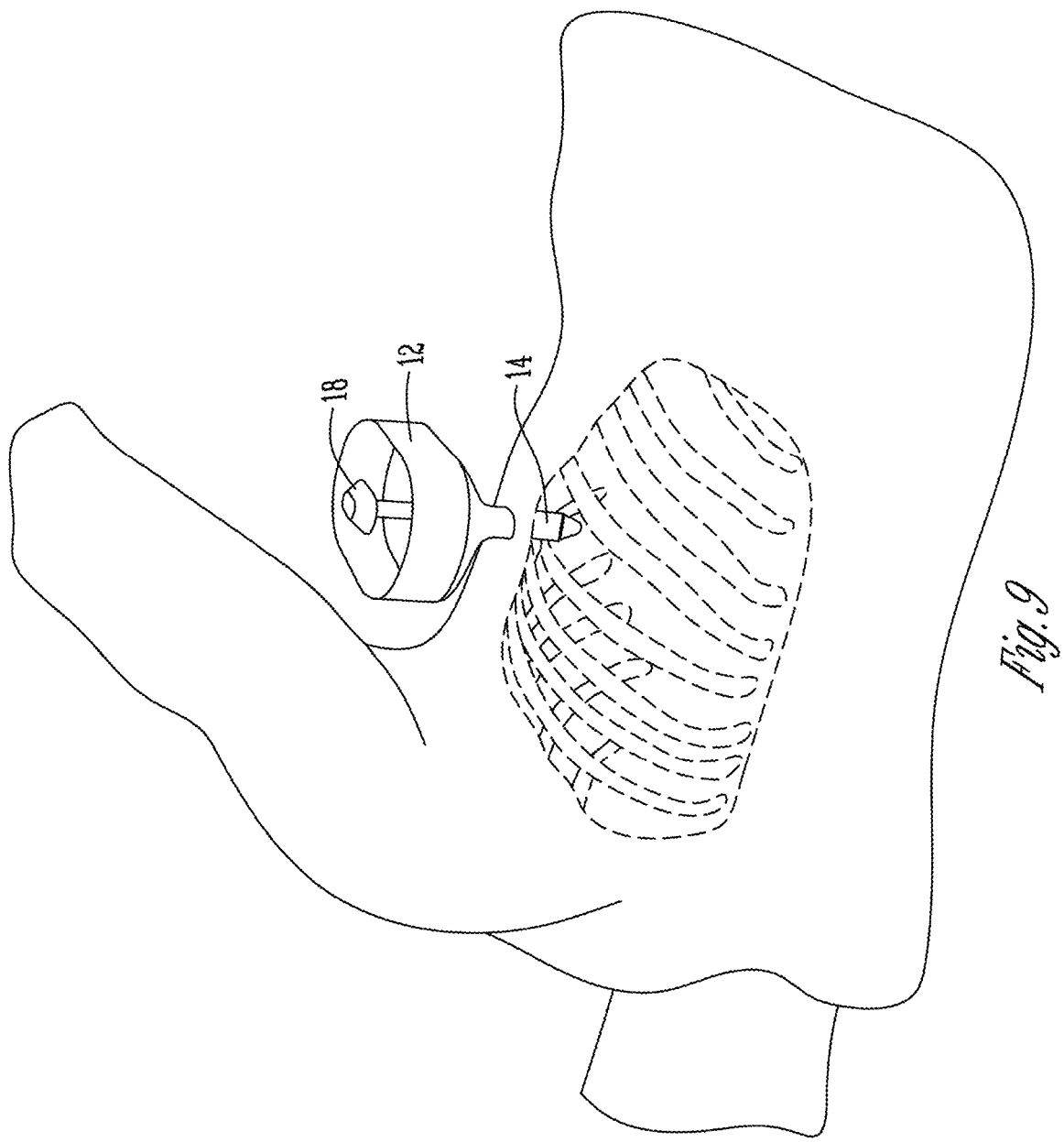

THORACOSCOPIC IRRIGATION CANNULA

CROSS-REFERENCE TO RELATED APPLICATIONS

This application claims priority to Provisional Application U.S. Ser. No. 62/620,175, filed Jan. 22, 2018, which is herein incorporated by reference in its entirety.

FIELD OF THE INVENTION

The invention is directed toward an irrigation cannula for use during thoracoscopic surgery, and particularly to a cannula for providing irrigation solution to the chest cavity during surgery.

BACKGROUND OF THE INVENTION

During chest surgery, it is sometimes necessary to fill the pleural space with a large volume of irrigation solution in order to check for bronchial stump leaks, or to facilitate cleaning and evacuation of debris and other biologic substances from the chest cavity. There are no prior art devices which manually accomplish this irrigation function. Existing prior art devices for chest surgery require the use of power and have been expensive and complex.

Therefore, a primary objective of the present invention is the provision of a thoracoscopic irrigation cannula for manually irrigating the chest cavity during chest surgery.

Another objective of the present invention is the provision of a thoracoscopic irrigation cannula which can rapidly deliver large volumes of solution to the pleural cavity through thoracoscopic surgical incisions between the ribs with minimal slippage.

A further objective of the present invention is the provision of a thoracoscopic irrigation cannula that is simple and safe to use, and easy to manufacture. For example, the need to provide a power source is eliminated.

These and other objectives will become apparent from the following description of the invention.

SUMMARY OF THE INVENTION

The thoracoscopic irrigation cannula of the present invention includes a bowl with a small diameter leg, and a drain opening at the juncture of the bowl and upper end of the leg. An obturator has an upper handle and a lower tip that is manually inserted through the leg to facilitate insertion of the leg through the incision in the chest wall. The thoracoscopic irrigation cannula can be made from a variety of materials, including metals and polymers. Also, the cannula can be disposable or reusable. The size of the bowl can also vary, for example, a smaller bowl for surgery on a child and a larger bowl for surgery on an adult. The shape of the bowl can also vary.

The cannula is operated manually, without electrical power, batteries, or other complex structure.

DESCRIPTION OF THE DRAWINGS

FIG. 9 is a view showing the cannula being inserted through an incision in the chest wall and into the chest cavity.

DETAILED DESCRIPTION OF THE INVENTION

Figure 1:
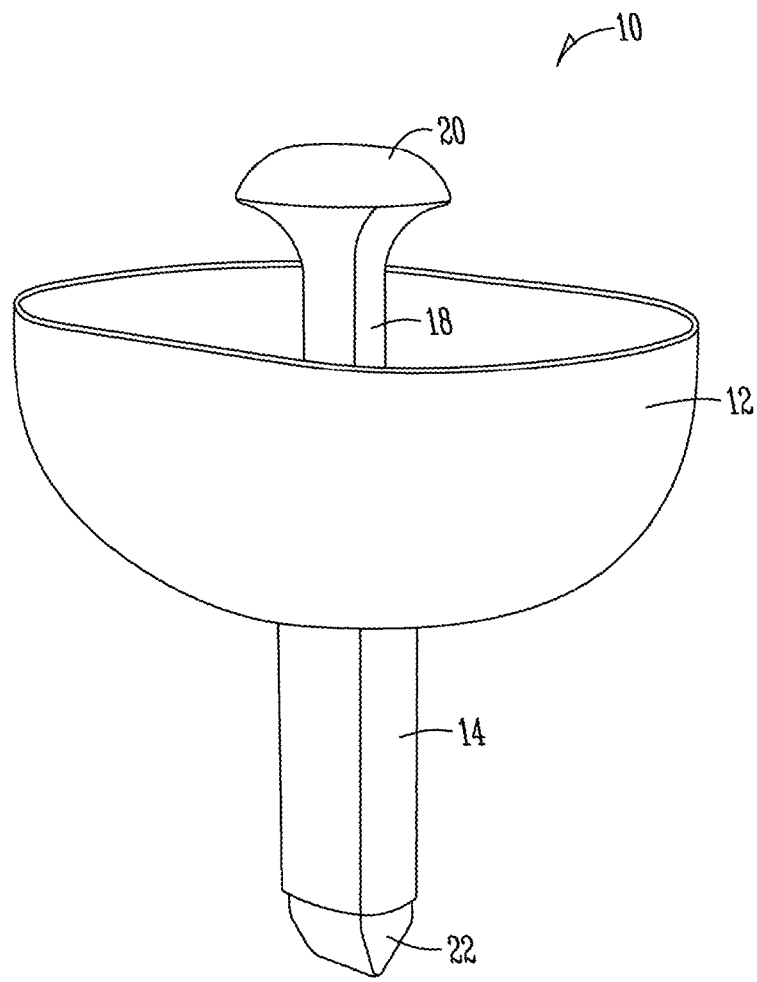
FIG. 1 is a perspective view of one embodiment of a thoracoscopic irrigation cannula of the present invention.
Figure 2:
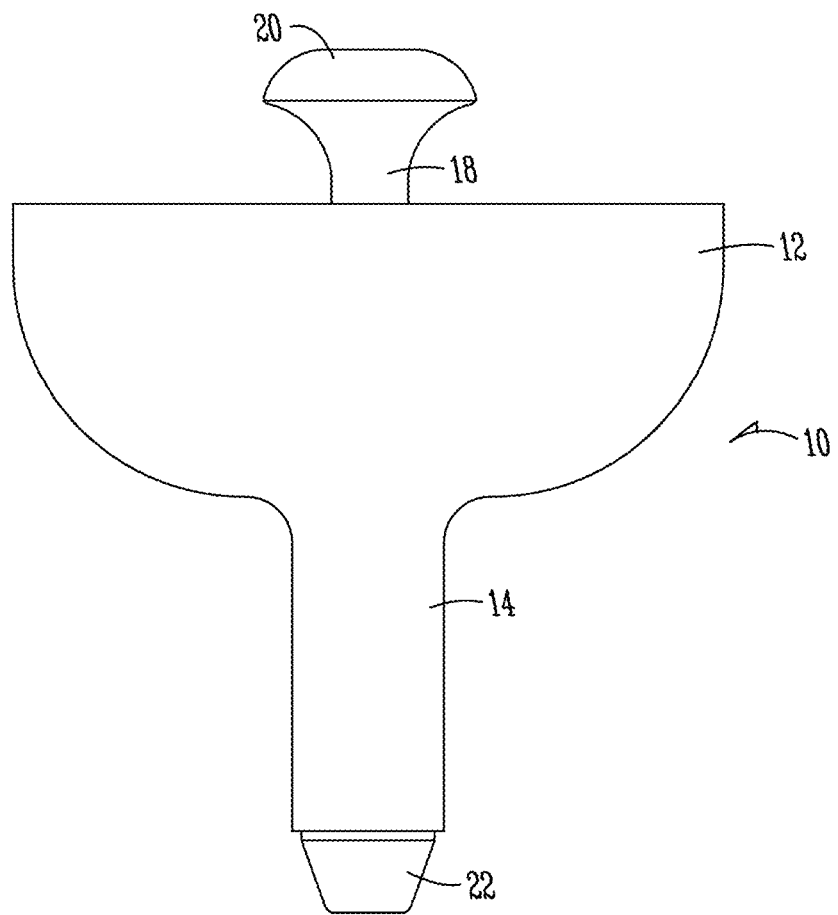
FIG. 2 is a side elevation view of the thoracoscopic irrigation cannula shown in FIG. 1.
Figure 3:
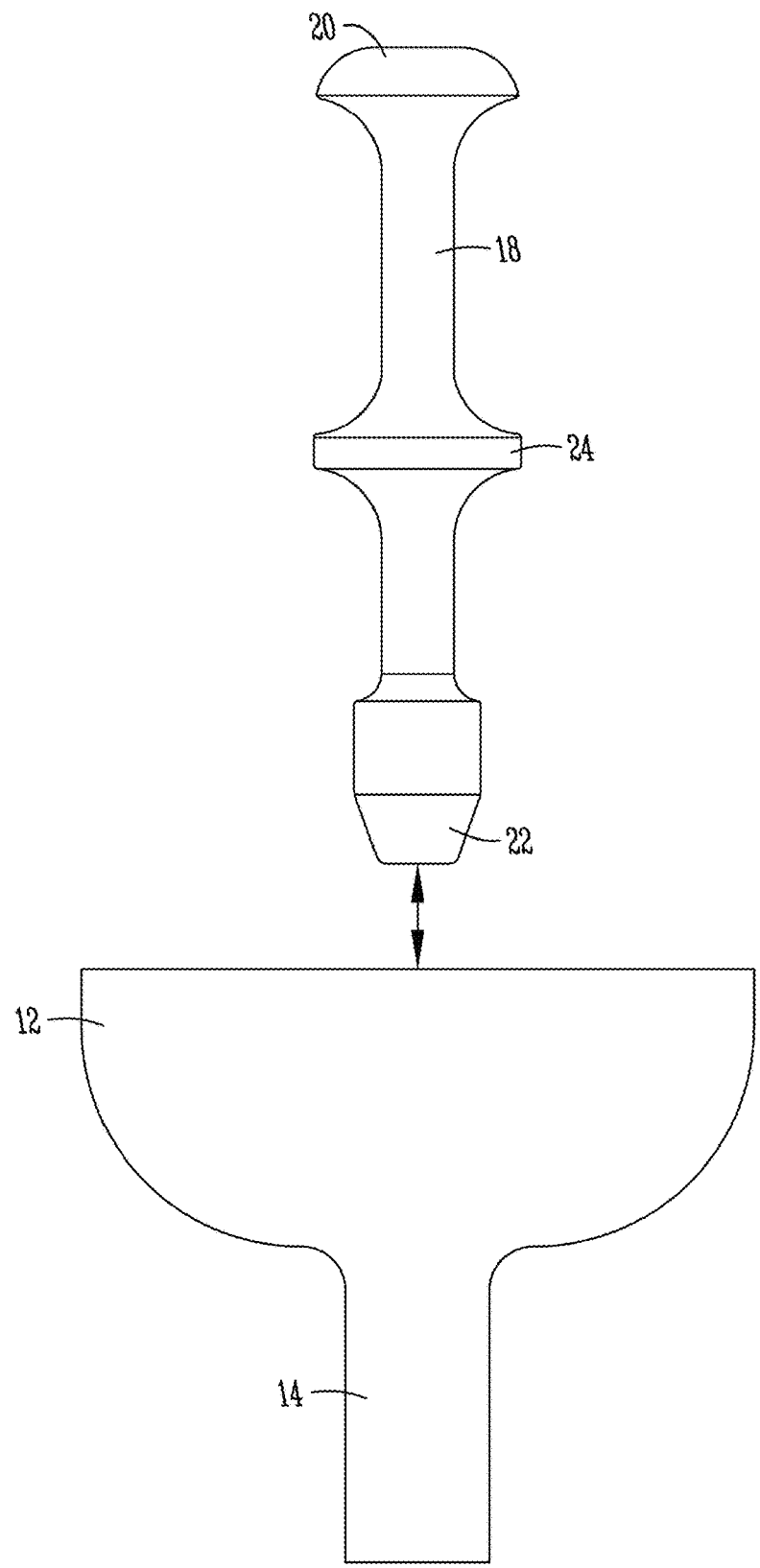
FIG. 3 is a side elevation of the thoracoscopic irrigation cannula with the obturator removed from the bowl.
Figure 4:
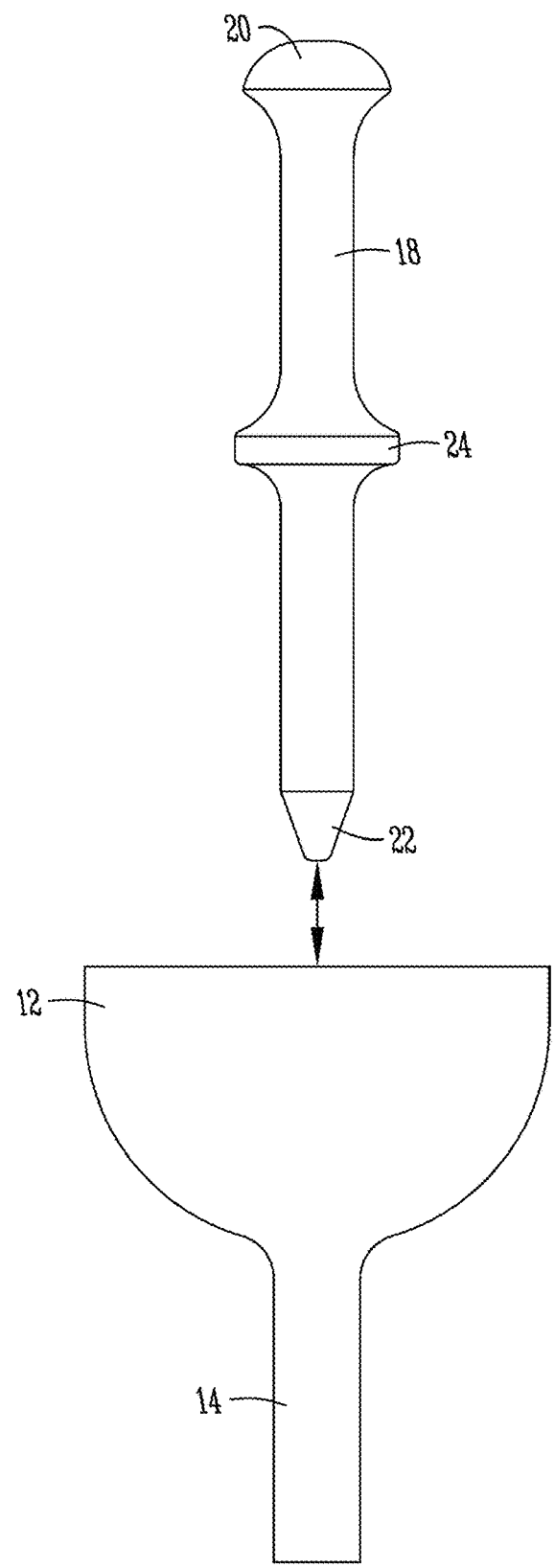
FIG. 4 is an end elevation view of the bowl and obturator.

The thoracoscopic irrigation cannula of the present invention is generally designated by the reference numeral 10 in the drawings. The thoracoscopic irrigation cannula includes a bowl 12 and a hollow leg 14 connected to the bowl 12. Preferably, the bowl 12 and leg 14 have an integral construction. The bowl 12 includes a drain opening 16 which allows liquid in the bowl to drain through the leg 14.

Figure 5:
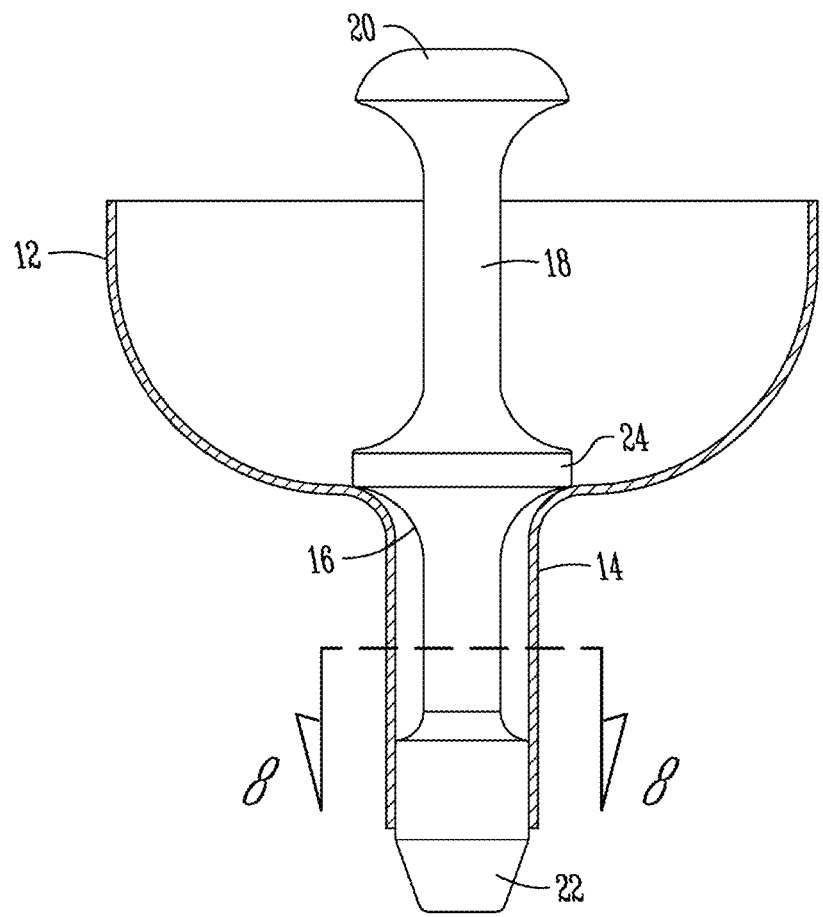
FIG. 5 is a sectional view showing the obturator in a first position engaging the drain opening of the bowl.
Figure 8:
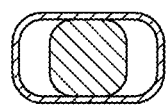
FIG. 8 is a sectional view along line 8-8 of FIG. 5.
Figure 6:
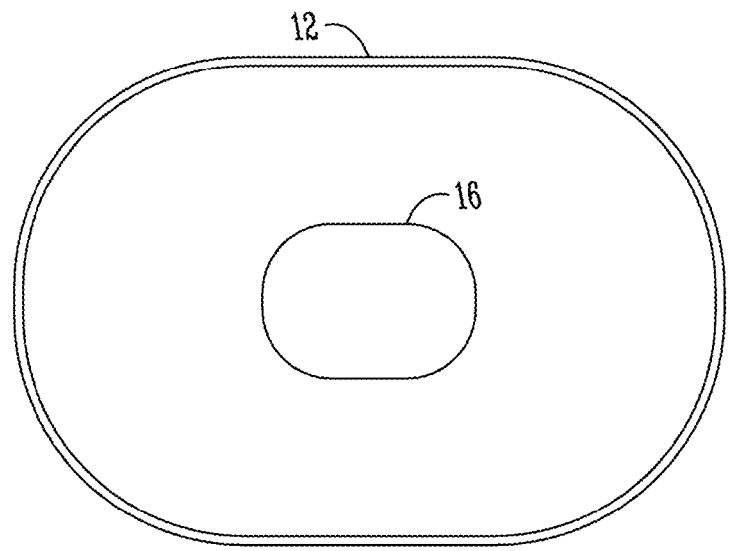
FIG. 6 is a top plan view of the bowl and obturator.
Figure 7:
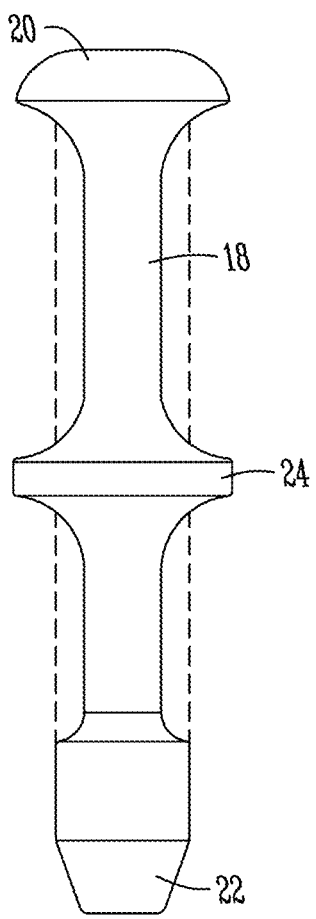
FIG. 7 is a side elevation view of the obturator shown in FIG. 3.

An obturator 18 is removably insertable into the leg 14 so as to facilitate insertion of the leg 14 though the chest incision into the chest cavity. The obturator 18 has an upper end 20 forming a handle which may extend above the bowl 12 and a lower end 22 which extends beyond the open end of the leg 14. In the preferred embodiment, the lower end 22 of the obturator 18 has a smooth, curved surface to facilitate passage of the leg 14 through the tissues around the incision. Preferably, the thoracoscopic irrigation leg 14, and obturator 18 have a round or oval cross section, as shown in FIG. 8. One of ordinary skill in the art will appreciate that the shape will depend upon the physical restrictions around the location of the incision. As shown in FIGS. 5 and 8, the outside diameter of the obturator 18 may vary but is smaller than the inside diameter of the leg 14, so that the tip of the obturator passes through the leg 14 easily.

In a preferred embodiment, the bowl 12 and leg 14 are formed as a one-piece integral unit. The bowl 12 and leg 14 can be made of various materials, including metal and plastic, and sterilized before use. The cannula 10 may be designed for one-time disposable use, or for re-use after sterilization. The leg 14 has a length for one-time disposable use, or for re-use after sterilization. The leg 14 has a length sufficient to extend through the incision in the chest wall and into the pleural space the chest cavity.

Figure 10:
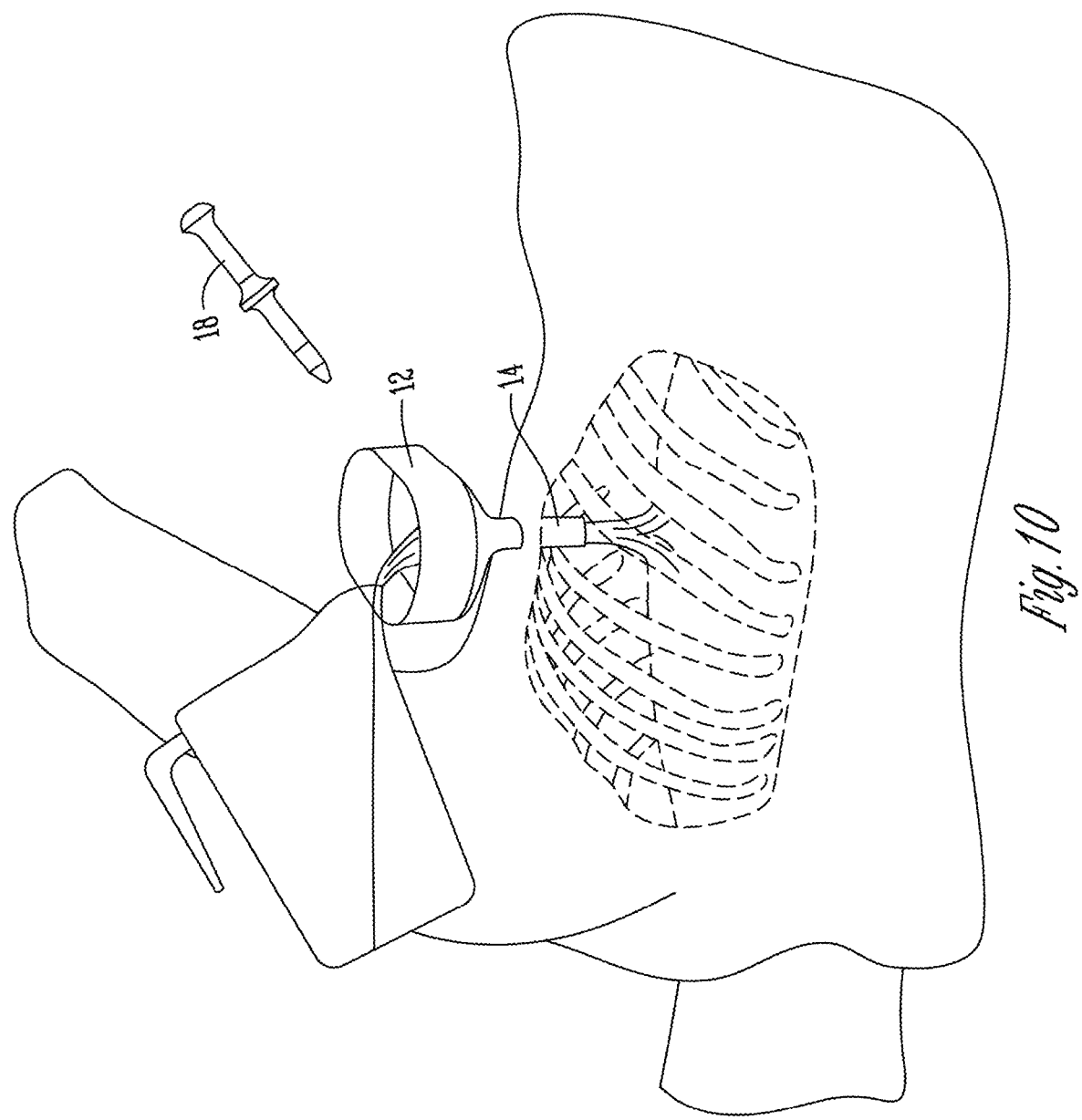
FIG. 10 is a view showing the cannula in use for supplying a liquid into the chest cavity.

In use, the obturator 18 is manually moveable between a first position fully inserted into the bowl 12 and through the leg 14, such that an enlarged diameter plug portion 24 stops at the drain opening 16, so as to limit how far the lower end of obturator 22 extends beyond the end of the leg tip 14 to assure smooth introduction through the incision. The handle 20 can be held by the operator to facilitate guidance of the cannula into the chest cavity. There is smooth transition between the lower end of obturator 22 and end of the cannula in the inserted position, to decrease resistance during passage through the tissues of the incision. When the cannula 14 is passed through the incision into a desired position into the chest, the operator holds the handle 20 of the obturator 18 and manually pulls the obturator upwardly or outwardly from the bowl 12. Then the solution can be poured into the bowl 12 for drainage through the leg 14 into the chest cavity, as shown in FIG. 10.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A thoracoscopic irrigation cannula, comprising:
   a bowl with an open top through which an irrigation liquid is added to the bowl and a lower drain opening;
   a hollow leg connected to the bowl beneath the drain opening, and sized for insertion through a body incision; and
   an obturator having upper and lower ends, and being manually movable between a first position wherein the lower end extends downwardly into the leg and the upper end resides above the top of the bowl, a second position wherein the lower end is removed from the leg by pulling upwardly on the upper end to allow the liquid in the bowl to drain by gravity through the drain opening and the leg into a chest cavity of a patient.

2. The thoracoscopic irrigation cannula of claim 1 wherein the obturator has an upper end residing above the bowl.

3. The thoracoscopic irrigation cannula of claim 1 wherein the obturator has a lower end extending beyond the leg in the first position.

4. The thoracoscopic irrigation cannula of claim 3 wherein the lower end of the obturator has a rounded tip extending out of the leg when the obturator is in the first position.

5. The thoracoscopic irrigation cannula of claim 1 wherein the obturator has upper and lower ends, and an enlarged plug portion between the upper and lower ends.

6. The thoracoscopic irrigation cannula of claim 5 wherein the lower end is rounded.

7. The thoracoscopic irrigation cannula of claim 5 wherein the lower end extends beyond the leg when the obturation is in the first position.

8. The thoracoscopic irrigation cannula of claim 2 wherein the upper end of the obturator extends above the bowl when the obturator is in the first position.

9. The thoracoscopic irrigation cannula of claim 1 wherein the obturator is formed as one piece.

10. The thoracoscopic irrigation cannula of claim 1 wherein the bowl and leg are formed as one piece.

11. The thoracoscopic irrigation cannula of claim 1 wherein the obturator has upper and lower ends, and an enlarged diameter mid-portion between the upper and lower ends, with the mid-portion being adapted to engage the drain opening of the bowl.

12. The thoracoscopic irrigation cannula of claim 1 wherein the cannula is free from a power source.

13. The thoracoscopic irrigation cannula of claim 1 wherein the cannula is free from an electrical connection.

14. A method of irrigating a chest cavity during thoracoscopic surgery, comprising:
   making an incision in a chest wall of a patient;
   manually inserting an obturator through a hollow lower hollow leg of a cannula to seal the leg and an upper end of the obturator resides above an upper end of the cannula;
   inserting the leg through the incision and into the chest cavity;
   introducing irrigation solution into the bowl through an open top of the bowl; and then
   manually pulling upwardly on the upper end of the obturator to remove the obturator from the leg to allow the irrigation solution to drain by gravity flow out the leg and into the chest cavity.

15. The method of claim 14 wherein the insertion and removal of the obturator is performed by gripping an upper end of an obturator.

16. The method of claim 14 wherein insertion of the obturator is limited by an enlarged diameter portion between an upper handle and a lower tip of the obturator.

17. The method of claim 14 further comprising sterilizing the cannula before use.

18. The method of claim 14 further comprising disposing of the cannula after one use.

19. The method of claim 14 further comprising sterilizing the cannula after each use.

20. The method of claim 14 wherein the cannula is free from connection to electricity.

* * * * *